United States Patent [19]
Mehl, Sr. et al.

[11] Patent Number: 5,766,214
[45] Date of Patent: Jun. 16, 1998

[54] MELANIN ENHANCED PHOTOTHERMOLYSIS HAIR REMOVAL

[76] Inventors: Thomas L. Mehl, Sr., 1015 Rte. 1, Hwy. 337, Newberry, Fla. 32699; Nardo Zaias, 1015 W. 47 Ct., Miami Beach, Fla. 33140

[21] Appl. No.: 634,569

[22] Filed: Apr. 18, 1996

[51] Int. Cl.$^6$ .................................. A45D 26/00
[52] U.S. Cl. .................. 606/9; 607/88; 607/89; 606/133
[58] Field of Search .................. 606/9–12, 36, 606/131, 133; 607/1, 88–89; 128/898

[56] References Cited

U.S. PATENT DOCUMENTS

| | | | |
|---|---|---|---|
| 5,059,192 | 10/1991 | Zaias | 606/9 |
| 5,065,515 | 11/1991 | Iderosa | 606/9 |
| 5,226,907 | 7/1993 | Tankovich | 606/9 |
| 5,286,979 | 2/1994 | Berliner et al. | 250/515.1 |
| 5,411,741 | 5/1995 | Zaias | 424/450 |
| 5,425,728 | 6/1995 | Tankovich | 606/9 |

FOREIGN PATENT DOCUMENTS

WO95/15725  6/1995  WIPO.

*Primary Examiner*—Jennifer Bahr
*Assistant Examiner*—Rosiland Kearney
*Attorney, Agent, or Firm*—Sven W. Hanson

[57] ABSTRACT

A method of permanent hair removal which uses a high energy light source projected at the skin to cause death of the hair follicle by photothermolysis. The process uses either incoherent or coherent light energy. Additional melanin is added to the skin by a process which delivers the melanin to the region of the hair follicle thereby enhancing that area as a light absorbing target. Collateral damage to the surrounding skin tissue is minimized. The delivery process uses liposomes selected particularly to encapsulate and carry melanin to the target region. The invention also encompasses a general method of deleterious tissue destruction by selective introduction of melanin and subsequent photothermolysis.

9 Claims, 1 Drawing Sheet

MELANIN ENHANCED PHOTOTHERMOLYSIS HAIR REMOVAL

FIELD OF THE INVENTION

This invention relates to methods of permanent hair removal by photothermolysis. Specifically, methods of hair method are disclosed wherein the absorption of light energy used to kill the hair follicle and germative cells is enhanced by introducing additional melanin into the hair follicle, the surrounding tissue, and hair itself using a liposome based delivery system.

BACKGROUND OF THE INVENTION

Photothermolysis as a method of hair removal can be divided into two general methods. The first being essentially the application of laser energy selected to be absorbed preferentially by elements residing naturally in the proximity of the hair follicle (see Zaias - U.S. Pat. No. 5,059,192). The second being differentiated from the first by introduction of a foreign element to provide a radiation target with an absorption frequency different from the naturally occurring elements (see Tankovich - U.S. Pat. Nos. 5,226,907 and 5,425,728). In both cases death of the hair follicle is caused by localized thermolysis and subsequent destruction of the living tissue. One objective of any method of laser depilation is to minimize the radiation absorption of the surrounding skin and thereby reduce collateral damage.

A limitation of the second method, that of applying laser light by which natural skin and hair elements are not energized, is the obvious restriction from potential use of many available laser light sources. Because melanin naturally occurring in the skin is generally darker in color than the surrounding skin cells and tends to absorb, to some extent, a broad range of frequencies of incident light energy, depilation methods which attempt to avoid excitation of such natural elements are greatly limited. This is also true of incoherent light sources. What is needed to broaden the range of useful light energy frequencies in permanent hair removal processes are methods which are not dependent upon avoiding the excitation of natural skin elements.

OBJECTS AND SUMMARY OF THE INVENTION

It is an objective of this invention to provide an improved method of permanent hair removal which uses light energy which is absorbed preferentially by naturally occurring elements surrounding the hair follicle to cause photothermolysis damage resulting in death of the hair producing tissue.

It is another object of the invention to provide a method of hair removal which increases the quantity of melanin surrounding the hair follicle to create an enhanced target for incident light energy and improve the preferential absorption in the proximity of the hair follicle.

It is another object of the invention to provide an improved method of laser hair removal which uses laser energy of a wavelength which is absorbed by naturally occurring elements in the skin.

It is a further object of the invention to provide a method of hair removal by photothermolysis which minimizes the required irradiation and thereby minimizes the damage to the surrounding skin.

It is also an object of the invention to provide a method of destroying cancer cells by photothermolysis by selective delivery of melanin using liposomes to create an enhanced target for subsequent application of light energy.

The present invention encompasses a depilation method which meets the above objectives by providing a system wherein the naturally existing elements surrounding the hair follicle, namely the melanin, are enhanced as a light energy receiving target. This is accomplished by preferentially depositing additional quantities of melanin at the follicle site or its proximity. This preferential deposition is effected by encapsulating a melanin compound in a liposome specifically selected and formed to penetrate the epidermis and bind to specific sites in the proximity of the hair follicle. In use, such a liposome or liposome carrying medium is applied topically to the skin. After the liposome has carried the melanin to the hair follicle site, laser energy of a frequency which is readily absorbed by the melanin is directed at the skin. As a consequence of the added quantity of melanin, a greater proportion of the incident light energy is absorbed at the hair follicle causing thermolysis and death of the hair follicle. Overall irradiation of the skin can be reduced while still effecting depilation due to the enhanced absorption at the follicle. With the above process the present invention can be used to cause permanent hair loss using a variety light energy sources, both coherent and incoherent, including such lasers as ruby red and Nd-YAG, alexandrite, and diode lasers, or any other light source providing an effective frequency and intensity. To effect energy absorption by melanin, the light energy should be in the wavelength range of 400 to 1500 nm.

The techniques of the invention are extended to delivery of melanin to other deleterious tissue. In this manner photothermolysis may be used to remove cancer cells.

These advantages as well as others will be apparent in the following description.

DESCRIPTION OF THE PREFERRED EMBODIMENTS

In using high energy light sources such as lasers on mammalian skin, it is preferable to use the minimal amount of treatment required to achieve the objective. As with chemical epidermal treatments, overdosage can cause unwanted scarring or damage. A ruby laser is preferred to produce the desired effect of depilation and eliminate hair regrowth.

However, to reduce the required exposure in using any laser, as well as other light sources, and thereby avoid producing unwanted side-effects, such as scarring, the following method of introducing additional melanin to the follicle region has been developed. In addition to reducing the required light energy exposure for effective hair removal, by increasing the relative absorption of the target, this method allows the use of laser light of wavelengths that would be otherwise excessively damaging to the surrounding skin. Prior to discussing a liposome delivery process for addition of melanin, the process of laser photothermolysis for depilation will first be detailed.

Using the process of selective photothermolysis, a laser wavelength is matched with the absorption spectrum of the melanin found at the base of the hair follicle. Melanin is a pigment which is concentrated at the base of the follicle and which has an absorption spectrum that is highest in the ultraviolet range and gradually diminishes toward the infrared. The depth of penetration of light is dependent on its wavelength and duration of pulse and longer wavelengths are required to damage the hair follicle deep in the dermis as well as germative tissue in the bulge region.

Therefore, the depth of penetration can be selected through the selection of an appropriate wavelength, desired pulse duration and the damage at a particular depth is controlled by the energy applied. Of course, as higher energy levels are used, the depth of penetration will be increased through the generation and accumulation of heat through absorption. A careful balance of the laser parameters leads to destruction of the hair follicle without permanently destroying normal adjacent epidermal and dermal structures.

Figure 1:
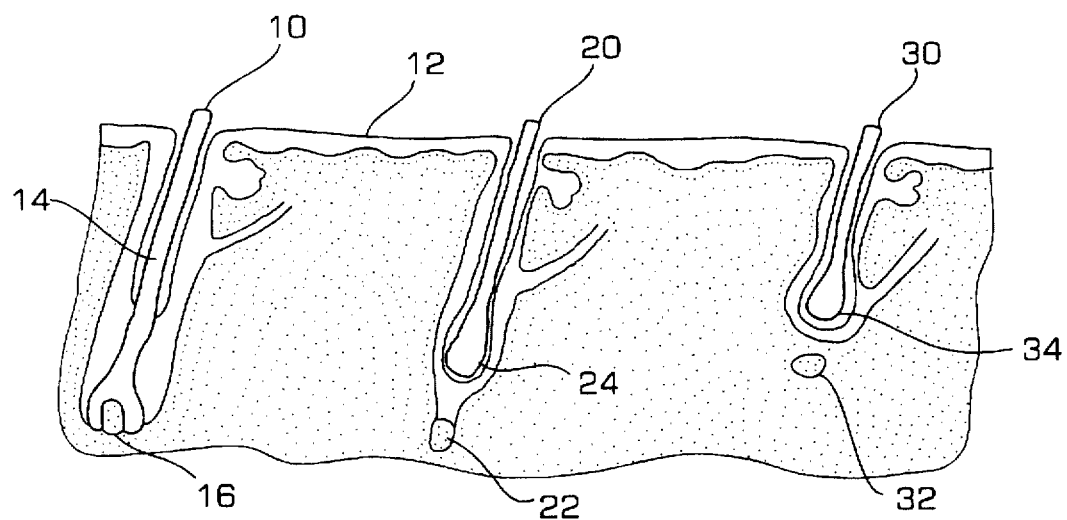
FIG. 1 is a cross-sectional view of three hair shafts showing the stages of the hair cycle.

FIG. 1 shows a hair shaft 10 which has been cut down to the near the surface of the skin 12. The shaft 10 extends down to the follicle 14 which at the anagen stage of the hair cycle joins the papilla 16. It is generally accepted that destruction of the papilla 16 is necessary to prevent hair regrowth. After growing for about three years in the anagen stage, the hair shaft 10 enters the catagen stage represented by hair shaft 20 wherein the papilla 22 separates from the base of the follicle 24. The catagen stage lasts only a few weeks.

Hair shaft 30 represents the telogen stage of the hair cycle wherein the papilla 32 completely separates from the follicle 34 and forms a new secondary hair germ which will repeat the cycle. The telogen stage lasts about three months.

In order to assure sufficient injury to the papilla 32 at the telogen stage as well as the papilla 16 at the anagen stage, use of a light source with sufficient energy and depth of penetration is usually necessary to achieve sufficient melansomal destruction.

Cutting of the hair shaft 10 down to the skin 12 provides two important functions of the treatment process. First, the tip 18 of the hair shaft 10 allows the operator to position the light source substantially vertically over the hair follicle opening such that an optimum location for aiming the light energy to strike the papilla 16 is obtained. Second, the reduction of excess hair eliminates additional scattering of the radiant energy contained.

Figure 2:
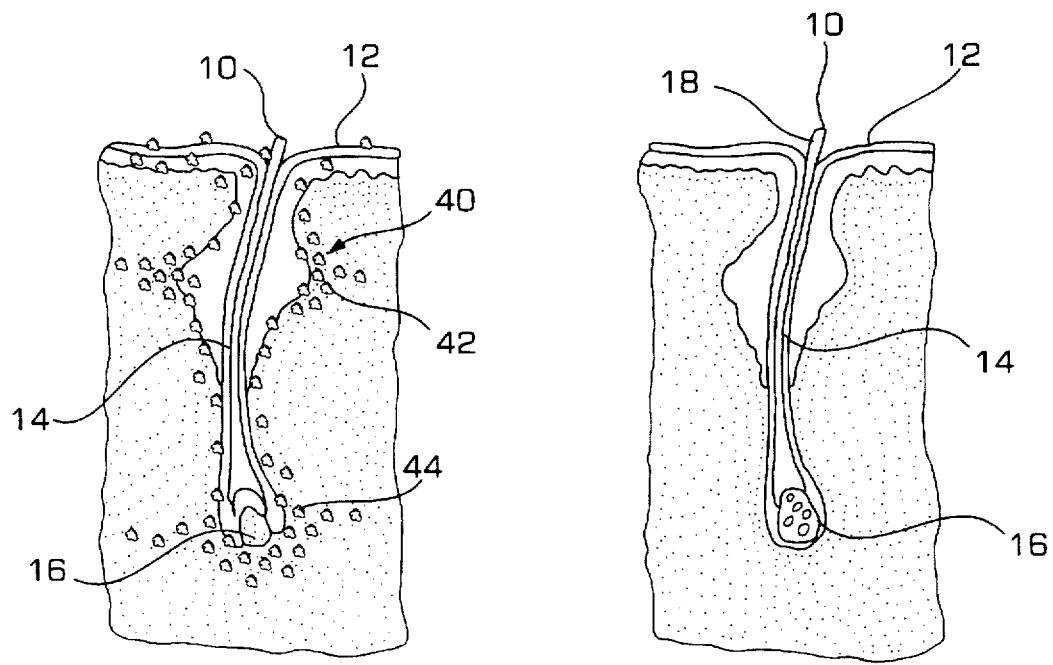
FIG. 2 is a cross-sectional view of a hair follicle after the top has been cut, but prior to application of light energy. Liposomes are shown and distinguished in the bulge and papilla regions.

FIG. 2 shows an enlarged view of the hair shaft 10 prior to treatment, wherein the follicle 14 and papilla 16 are normal in appearance in the anagen stage.

Figure 3:
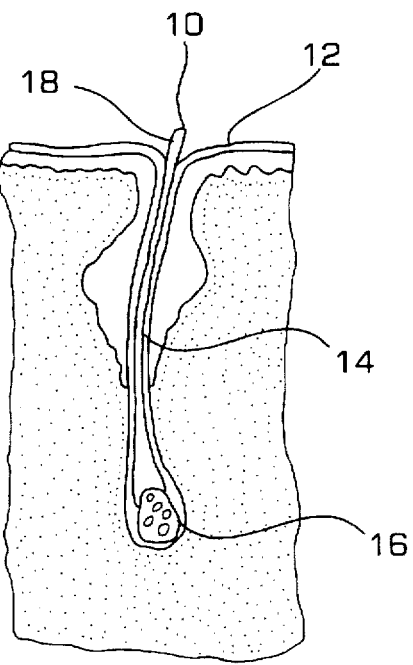
FIG. 3 is a cross-sectional view of the follicle of FIG. 2 after exposure to light energy treatment, showing the damaged hair germ.

FIG. 3 show the treatment after the light energy has been applied to the follicle 14 and the resulting effect on the papilla 16.

Application of the laser pulse to the follicle and the papilla causes photothermolysis which provides melanosomal disruption, including vaporization of the melanin in the follicle 14 and papilla 16, as well as vacuolation, edema, gas bubbles and protein denaturation. When the radiation absorbed is of sufficient energy level, these effects seriously injure the hair follicle and papilla, thereby damaging the hair germative cells which causes hair regrowth.

The hair follicle 14 may extend into the reticular dermis up to 3 mm from the skin surface. In order to achieve the depth of penetration required to destroy the hair follicle 14, it has been found that a wavelength of about 694 nm, which is produced by the ruby red laser, is preferred. The ruby red laser tends to produce less severe dermal injury.

Where the hair follicle has not been enhanced by addition of melanin, or other enhancing compound, the degree of follicular injury is solely dependent on the radiant exposure dose to the existing melanin. Without melanin enhancement, follicular damage is first observed at as low as 0.4 J/cm2. At such a low dose, the hair may fall out of the skin. However, normal regrowth will soon occur. Scarring has been found to occur at about 10 J/cm$^2$. While an exposure dose of 8.0 J/cm$^2$ has previously been found to be optimum, with the enhancement of the target follicles with liposome delivered melanin, the required effective doses may be reduced.

The upper limit of exposure dose for laser hair removal is set by collateral damage to the surrounding skin. To improve the effectiveness of applied light energy in causing hair follicle death, the present invention introduces additional melanin to the hair follicle region to enlarge the effective target. In this manner a greater portion of the incident energy is directed to death of the hair follicle and germative cells.

Although the above description has been principally in terms of lasers as the light energy source producing photothermolysis, incoherent light sources can be similarly applied so long as the wavelength and intensity of light produced meets the above requirements. In the same vain, it is possible to control pulsed, continuous wave, and q-switched lasers as well as others to effect photothermolysis of germative cells in this process. An example of such a light source in a therapeutic application is provided in U.S. Pat. No. 5,344,434 to Talmore.

To accomplish the preferential delivery of melanin to the hair follicle a liposome based system has been developed. Liposomes have the combined benefits of providing an encapsulating and carrying means as well as being able to be structured for selective delivery of its contents.

Liposomes provide a non-toxic means for encapsulation and can be further modified to bind to specific sub-populations of cells. Specifically, the liposome membranes according to the present invention can be made to bind to specific sub-populations of the basal cell region in the proximity of the hair follicle thereby increasing efficiency and specificity of melanin delivery. There are currently two theories regarding the optimum target region for thermolysis as a means of preventing hair regrowth. The generally accepted theory is that destruction of cells at the depth of the papilla is required to prevent cells in the telogen stage from forming new hair. The above description of depilation is generally based on this presumption. However, a second theory is that regrowth may be prevented by destruction of cells no deeper than the "bulge" region 40 depicted in FIG. 2. Liposomes in the present invention can be selected to bind preferentially to cells in either, or both, of the bulge and papilla regions. In this way, laser depilation under either theory may be enhanced by the introduction of melanin into the target region. In FIG. 2, liposomes (42 and 44) in both the "bulge" region and in the papilla region are shown.

Liposomes have also been previously used to encapsulate melanin for introduction into non-pigmented human fibroblast. See "Polyethylene-Glycol-mediated Delivery of Liposome-entrapped Pigments into Fibroblasts: Experimental Pigment Cells as Models for Mutator Phenotypes" by S. Schmitz, T. M. Allen and K. Jimbow in CANCER RESEARCH, 1992, Vol. 52, pp. 6638–6645.

Liposomes are microscopic spherical membrane-enclosed vesicles or sacs made artificially in the laboratory by a variety of methods. The primary requirements according to the present invention are that the liposomes should not be toxic to the living cells and that they should preferentially bind to, or otherwise be constrained to, the hair follicle vicinity. The liposomes according to the present invention may be of various size and may comprise either one or several membrane layers separating the internal and external compartments. An important element in liposome structures is that the liposome be resistant to destruction as it travels from the surface of the skin down to the target region. Liposome structures according to the present invention include small unilamellar vesicles (less than 250 angstroms in diameter), large unilamellar vesicles, and multilamellar vesicles.

The liposomes according to the present invention may be made from natural and synthetic phospholipids, glycolipids and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activities.

The liposomes of the present invention may be prepared by combining a phospholipid component with an aqueous component containing the selected melanin compound under conditions which will result in vesicle formation. The phospholipid concentration must be sufficient to form lamellar structures, and the aqueous component must be generally compatible with the melanin compound to be encapsulated. Methods for combining the phospholipid and the aqueous components so that vesicles will form include: drying the phospholipids onto glass and then dispersing them in the aqueous components; injecting phospholipids dissolved in a vaporizing or non-vaporizing organic solvent into the aqueous component which has previously been heated; and dissolving phospholipids in the aqueous base with detergents and then removing the detergent by dialysis. The liposomes can be produced from the foregoing mixtures either by sonication or by dispersing the mixture through either small bore tubing or through the small orifice of a French Press. The methods for producing the liposomes as set forth in U.S. Pat. No. 5,077,211 to Yarosh are incorporated herein by reference.

It is within the scope of the present invention to use other methods for encapsulating melanin within a liposome. A specific example of producing the liposomes would include the following process. A lipid mixture as set forth above is dissolved in an organic solvent and dried to a thin film in a glass vessel. The selected melanin compound is purified and added to the vessel at high concentrations in an aqueous buffer to rehydrate the lipid. The mixture is then agitated by vortexing and sonicated to form liposomes. The liposome spheres containing the encapsulated melanin compound are then separated from the unincorporated melanin compound by centrifugation or gel filtration.

A similar process for producing liposome encapsulated melanin is provided in the above work by Allen and Jimbow. In that process, liposomes are formed of a egg phosphatidylcholine and cholesterol mixture and then repeatedly extruded through polycarbonate membranes to increase uniformity of size. The unencapsulated melanin was removed by gel filtration. Generally, uniformity of size is not critical in delivery of melanin for the present invention. However, use of smaller liposomes may be advantages due to increased stability. This method in incorporated by reference.

The prepared liposome encapsulated melanin is administered to the hair follicle by topical application to the skin. Administration to humans requires that the liposomes be pyrogen-free and sterile. To eliminate pyrogens, pyrogen-free raw materials, including all chemicals as well as the melanin compounds and water are used to form the liposomes. Sterilization can be performed by filtration of the liposomes through a 0.2 micron filter. An effective concentration of liposomes is then suspended in a buffered polymeric glycol gel carrier for even application to the skin. In general, the gel carrier should not include non-ionic detergents which can disrupt the liposome membranes. Other similar vehicles can also be used to topically administer the liposomes. The concentration of the melanin in the final preparation can vary over a wide range and the desired concentration will depend upon parameters such as the laser light to be applied and the nature of the target skin and hair.

A general discussion of liposomes and liposome technology can be found in a three volume work entitled Liposome Technology edited by G. Gregoriadis, 1993, published by CRC Press, Boca Raton, Fla. The pertinent portions of each of these references are incorporated herein by reference.

Melanin, and melanin compounds, as used herein, refer to the family of compounds which exist naturally as the coloring pigment in mammalian skin and hair.

After the hair follicle region has been enhanced with melanin deposited liposomes, the skin is exposed to high intensity light energy. While the ruby red laser produces a preferred light energy in that it matches well the absorption range of melanin, the enhancement of the hair follicle as a target makes possible use other light frequencies. Diode lasers within the proper frequency can be used with similar effectiveness when configured to provide for sufficient power. Laser light such as produced by lasers other than the ruby red laser is not absorbed as readily by the natural melanin and surrounding skin. The consequence is unacceptable scarring. However, after the hair follicles have been enhanced with melanin by the above process the overall exposure can be reduced sufficiently to reduce or eliminate scarring such that a broad range of light sources can be successful employed in effecting permanent hair loss. As a result the present method may be successfully applied using any light source producing light of a frequency readily absorbed by melanin. The applicable wavelength range is about 400 to 1500 nm. This includes lasers commonly known as the ruby red, Nd-Yag, alexandrite, and diode lasers.

The selective delivery capabilities of liposomes can be used to extend the above process to other applications. By properly selecting and preparing an encapsulating liposome, melanin or other light absorption enhancers can be directed at other tissue such as cancer cells. In this manner, when removal of cancer cells or other deleterious tissue is required, application of liposome encapsulated melanin can increase the tissue's absorptivity of incident light and thereby enhance the tissue as a photothermolysis target. Application of a high energy light source will then cause photothermolysis of the cancerous tissue while damage to the surrounding skin is reduced. Similarly, where destruction of any particular tissue is desired, preferential photothermolysis can be effected by delivery of melanin to the area of interest by a appropriately selected liposome carrier followed by application of high energy light. Skin tissue effected by psoriasis can be similarly treated by the same process although the light energy applied is lessened to reduce the extent of tissue destruction.

The present technology can be further extended to processes for the dyeing of hair. The present processes can be used to deliver additional melanin coloring to the hair. Application of light energy of a intensity and total energy level below that causing photothermolysis can be used to release and affix the melanin in the tissue.

While this invention has been described as having a preferred method, it is understood that it is capable of further modifications, uses and/or adaptions and that these and such departures from the present disclosure as have come within known or customary practice in the art fall within the scope of the invention or the limits of the claims appended hereto.

We claim:

1. A method of permanent hair removal, comprising the steps of:

a. applying liposome encapsulated melanin to a skin area, b. aligning a light source over said skin area, and c. applying to said skin area light energy of sufficient energy and duration to damage the papilla so that hair regrowth is prevented, said light energy being of a wavelength which is readily absorbed by the melanin.

2. The method according to claim 1 wherein the light source is within the wavelength range of 400 to 1500 nm.

3. The method according to claim 1 wherein said light source is a laser.

4. The method according to claim 3 wherein said laser light source is aligned substantially vertically over said skin area.

5. The method according to claim 3 wherein said laser is a ruby red laser.

6. The method according to claim 3 wherein said laser is a Nd-Yag laser.

7. The method according to claim 3 wherein said laser is a diode laser.

8. A method of permanent hair removal comprising the steps of:

a. selecting a liposome to carry melanin into the dermis from the skin surface and reside preferentially in the proximity of the hair follicle, b. encapsulating a melanin compound in said liposome, c. topically applying said liposome with encapsulated melanin to a skin area, d. aligning a laser light applicator over said skin area, and e. applying to said skin area laser light of a wavelength which is readily absorbed by the melanin adjacent the hair follicle and having a radiant exposure dose of sufficient energy and duration to damage the papilla so that hair regrowth is prevented.

9. A method of permanent hair removal comprising the steps of:

a. selecting a liposome to carry melanin into the dermis from the skin surface and reside preferentially in the proximity of the bulge area of the hair follicle, b. encapsulating a naturally occurring melanin compound in said liposome, c. topically applying said liposome with encapsulated melanin to a skin area, d. aligning a laser light applicator over said skin area, and e. applying to said skin area laser light of a wavelength which is readily absorbed by the melanin at the hair follicle and having a radiant exposure dose of sufficient energy and duration to damage cells in the region of the bulge area so that hair regrowth is prevented and scarring of the surrounding skin is avoided.

* * * * *